United States Patent [19]

Elkins et al.

[11] Patent Number: 5,314,543
[45] Date of Patent: May 24, 1994

[54] METHOD FOR CLEANING A PROSTHESIS BY HEATING IN A MICROWAVE OVEN

[75] Inventors: William E. Elkins; William K. Kerr; Louis M. Ohls, all of Tulsa, Okla.

[73] Assignee: DeBron International, Tulsa, Okla.

[21] Appl. No.: 8,473

[22] Filed: Jan. 25, 1993

Related U.S. Application Data

[62] Division of Ser. No. 681,563, Apr. 5, 1991, Pat. No. 5,201,411.

[51] Int. Cl.⁵ .............................................. B08B 7/00
[52] U.S. Cl. ........................................ 134/1; 134/19; 134/30; 134/42
[58] Field of Search ................ 134/1, 19, 26, 30, 42; 422/300, 301; 206/83, 804, 817

[56] References Cited

U.S. PATENT DOCUMENTS

| | | | |
|---|---|---|---|
| 646,135 | 3/1900 | Smith | 220/93 |
| 1,488,456 | 3/1924 | Harper | 206/804 |
| 1,676,090 | 7/1928 | Johnson | 422/301 |
| 2,122,583 | 7/1938 | Parizot | 422/300 |
| 2,163,862 | 6/1939 | Wing | 422/301 |
| 2,252,654 | 8/1941 | Webber | 220/93 |
| 2,541,595 | 2/1951 | Marshall et al. | 206/83 |
| 2,929,117 | 3/1960 | Kosswig | 422/300 |
| 3,155,267 | 11/1964 | Swett | 220/93 |
| 3,275,133 | 9/1966 | Wood | 220/93 |
| 4,066,566 | 1/1978 | Lauster | 134/42 X |
| 4,179,040 | 12/1979 | Bateman et al. | 206/804 |
| 4,511,486 | 4/1985 | Shah | 134/42 X |
| 4,721,835 | 1/1988 | Welker | 210/155 X |
| 4,806,173 | 2/1989 | Toukan | 134/42 |
| 5,082,135 | 1/1992 | DeCoster | 220/93 |

FOREIGN PATENT DOCUMENTS 165311  2/1934  Switzerland .............. 422/300

*Primary Examiner*—R. Bruce Breneman
*Assistant Examiner*—Saeed T. Chaudhry
*Attorney, Agent, or Firm*—Dougherty, Hessin, Beavers & Gilbert

[57] ABSTRACT

A method for cleaning a prosthesis in a microwave oven. The inventive method preferably uses a container having an opening at the top thereof, a cover which is removably positionable over the opening, and a holding assembly removably positionable in the container, for holding the prosthesis. Since most prostheses contain at least somes metallic parts, the container and cover are each composed of a microwave insulating material. The inventive method provides for the quick and efficient cleaning of prostheses and facilitates the removal of dangerous fungal and bacterial deposits therefrom.

3 Claims, 2 Drawing Sheets

METHOD FOR CLEANING A PROSTHESIS BY HEATING IN A MICROWAVE OVEN

This is a divisional of copending application Ser. No. 07/681,563 filed on Apr. 5, 1991 U.S. Pat. No. 5,201,411.

BACKGROUND OF THE INVENTION

In one aspect, the present invention relates to devices for cleaning prostheses. In another aspect, the present invention relates to methods for cleaning prostheses.

It has been estimated that 60% of all denture wearers are troubled by chronic stomatitis or other fungal and/or bacterial conditions of the mouth. These fungal and bacterial conditions, which oftentimes lead to cancer, are in many cases caused and/or aggravated by fungal and bacterial build-up in the denture material. This fungal and bacterial build-up cannot be easily removed from the denture material using current conventional denture cleaning techniques. Thus, a need presently exists for a fast and effective means of (1) thoroughly cleaning prostheses and (2) eliminating fungal and/or bacterial build-up.

SUMMARY OF THE INVENTION

The present invention provides an apparatus for cleaning a prostheses. The apparatus comprises: a container having an opening at the top thereof; a cover which is removably positionable over the opening; and a holding means, removably positionable in the container, for holding the prosthesis. The container and the cover are each comprised of a microwave insulating material. The holding means preferably comprises two upwardly extending elongate members and a support member leaving a sloping upper surface. The support member is preferably connected to the elongate members such that the elongate members and the sloping upper surface of the support member form a restriction for gravitationally holding the prosthesis on the sloping upper surface and against the elongate members.

The present invention also provides a method of cleaning a prosthesis. The inventive method comprises the steps of: (a) placing the prosthesis, water, and an amount of denture cleanser sufficient for cleansing the prosthesis in a microwave insulating device and (b) heating the contents of the microwave insulating device in a microwave oven. The microwave insulating device used in the inventive method is preferably the inventive prosthesis cleaning apparatus.

The inventive apparatus and method can generally be used to clean any dental or facial prosthesis. Examples of such prostheses generally include: full dentures, partial dentures, any type of orthodontic appliance, maxillo facial prostheses, orthodontic tempro mandibular joint prostheses, and the like.

The inventive apparatus and method generally provide a fast and effective means for (a) thoroughly cleaning a prosthesis, (b) removing fungal and/or bacterial build-up therefrom, and (c) eliminating odor. By heating the cleaning system, (i.e., the prosthesis, water, and denture cleanser) in a microwave oven, a hot cleaning solution is quickly obtained. Increasing the temperature of the cleaning solution generally accelerates the cleaning activity of the denture cleanser. Additionally, heating the cleaning system in a microwave oven causes a desirable degree of molecular vibration to occur in the prosthesis and in the fungal and/or bacterial materials which have deposited on the prosthesis. As a result of this molecular vibration, the cleaning solution penetrates rapidly and deeply into the prosthesis and into the fungal and/or bacterial material.

In addition to the above, the inventive apparatus can generally be used to expedite, facilitate, and simplify any conventional (i.e., non-microwave) process for solution cleaning a prosthesis. The holding means of the inventive apparatus provides excellent cleaning fluid circulation during the cleaning process and greatly simplifies the rinsing, cooling, and drying processes which are typically performed after the cleaning process.

Other and further objects, features, and advantages of the present invention will be readily apparent to those skilled in the art upon reading the following description of the preferred embodiments.

DESCRIPTION OF THE PREFERRED EMBODIMENTS

Figure 2:
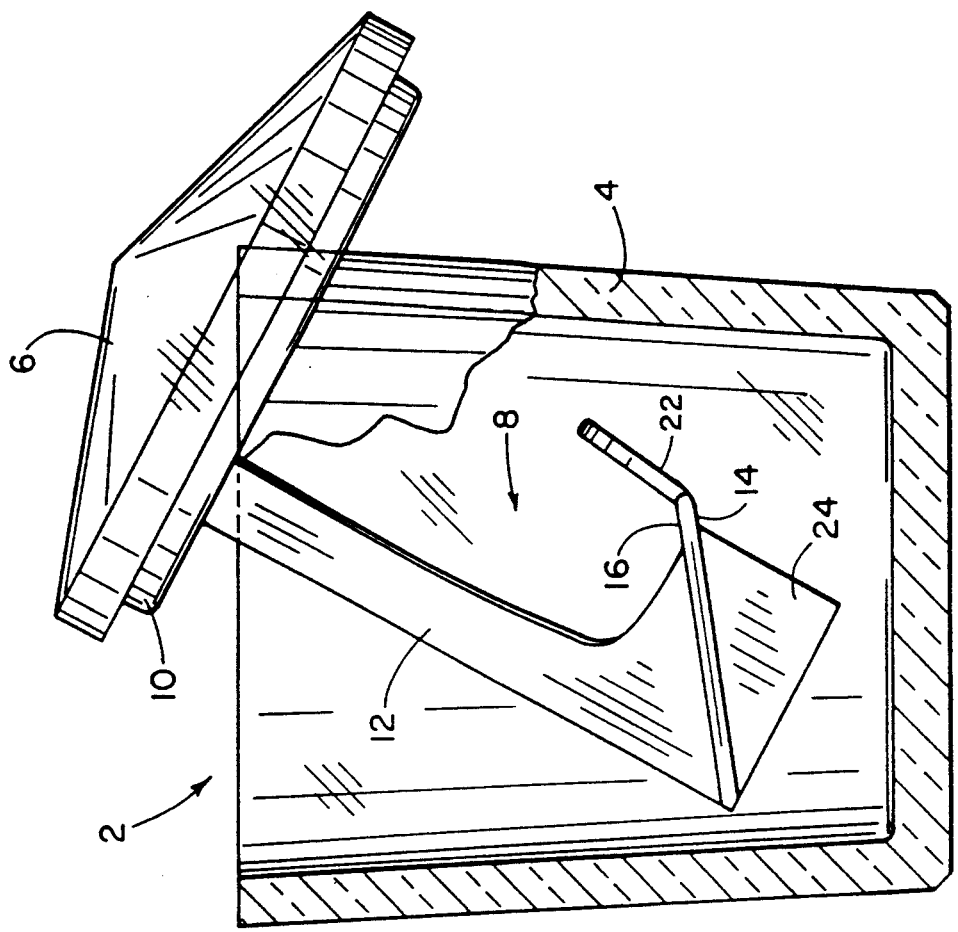
FIG. 2 provides an elevational side view of the inventive apparatus depicting the positionability and removability of cover 6 and prosthesis holding means 8.
Figure 1:
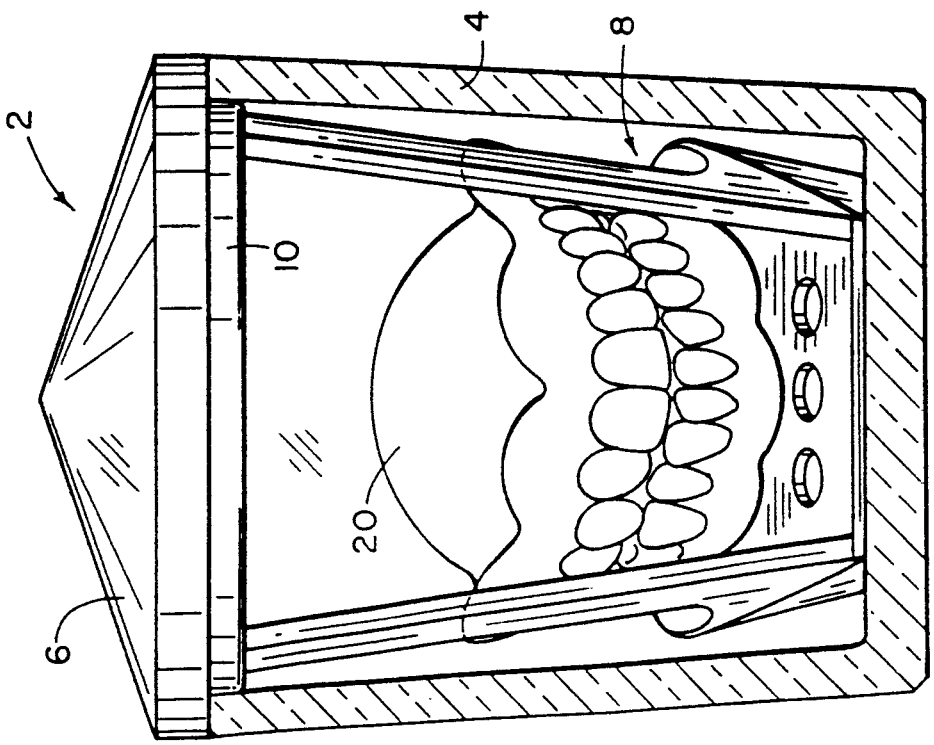
FIG. 1 provides an elevational front view of an embodiment 2 of the inventive apparatus.
Figure 3:
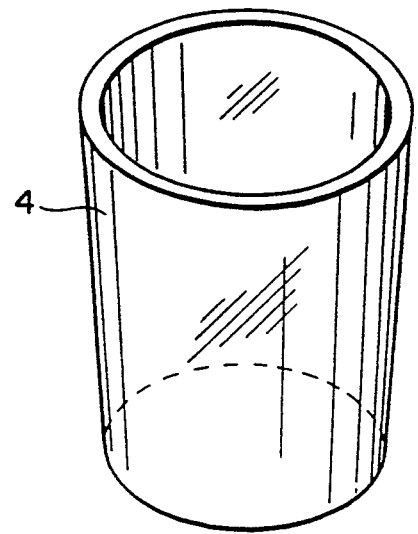
FIG. 3 provides a perspective view of container 4.

An embodiment 2 of the inventive apparatus is depicted in FIGS. 1-6. As shown in FIGS. 1-3, embodiment 2 generally comprises: a container 4 having an opening at the top thereof, a cover 6 which is removably positionable over the container opening, and a prosthesis holding means 8 which is removably positionable inside container 4. Since most prostheses typically contain metallic parts, container 4 and cover 6 are each preferably composed of a microwave insulating material. As used herein, the term "microwave insulating material" generally refers to any material in which a metallic object can be safely microwaved in a microwave oven. Due to its microwave insulating ability and its rugged durability, container 4, cover 6, and prosthesis holding means 8 are all preferably composed of polycarbonate.

Figure 4:
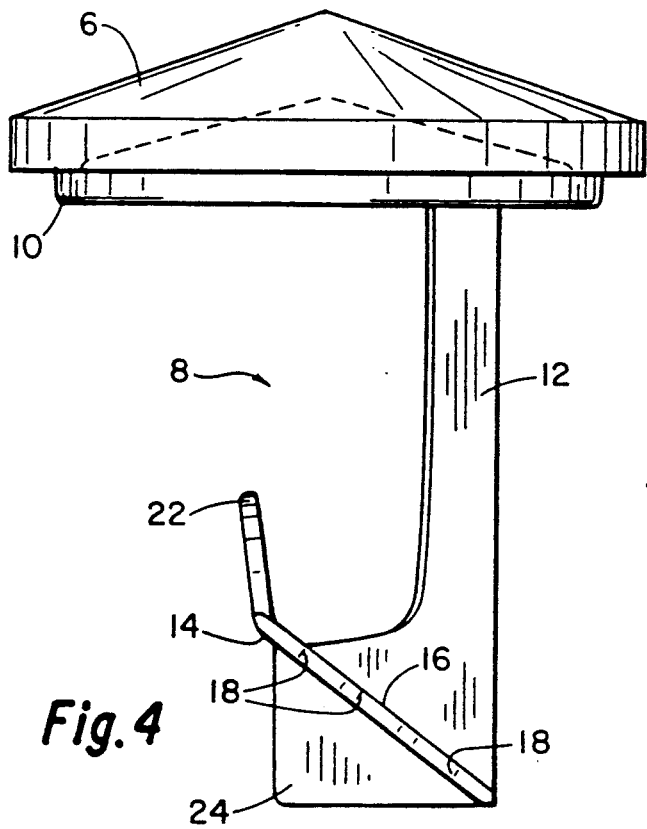
FIG. 4 provides an elevational side view of the cover and holding means 8.

As shown, for example, in FIGS. 1 and 4, a rim 10 is attached to the bottom of cover 6 near the outer edge of said cover. The outside diameter of rim 10 is slighly less than the inside diameter of the opening at the top of container 4. Thus, when cover 6 is positioned over the opening at the top of container 4, rim 10 fits inside the opening to help hold the cover securely on the container and to help seal the container.

Figure 5:
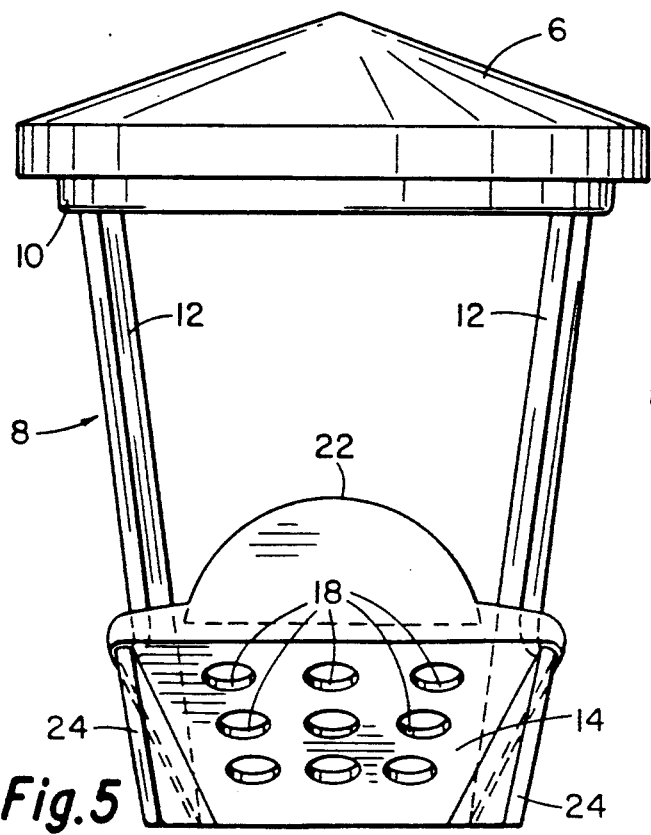
FIG. 5 provides an elevational rear view of cover 6 and holding means 8.
Figure 6:
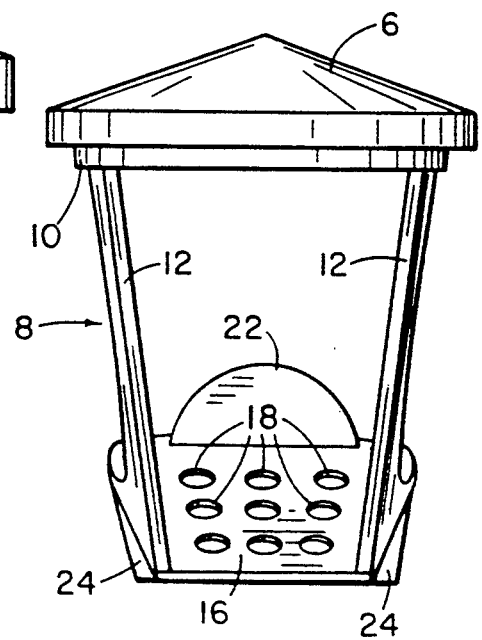
FIG. 6 provides an elevational front view of cover 6 and holding means 8.

Front, side, and back views of prosthesis holding means 8 are shown in FIGS. 4, 5, and 6. Prosthesis holding means 8 has two upwardly extending elongate members 12 and a sloping support member 14. Support member 14 has a planar upper surface 16. As shown in FIG. 6, the side ends of support member 14 are tapered such that support member 14 becomes narrower as it slopes downward. A plurality of apertures 18 extending through support member 14 and surface 16 facilitate fluid circulation, drainage, and drying.

As shown in FIGS. 1, 4, and 6, the bottom ends of elongate members 12 are attached to upper surface 16 at the side ends of support member 14. As shown in these figures, elongate members 12 and sloping support member 14 operate together to form a restriction wherein a prosthesis 20 can be gravitationally held on top of surface 16 and against elongate members 12. Consequently, prosthesis 20 can be placed in the restriction of holding means 8 so that the holding means and the prosthesis can be easily placed into and taken out of container 4. Holding means 8 can also be used to conveniently hold prosthesis 20 during subsequent rinsing and drying procedures.

Holding means 8 also includes means for preventing prostheses 20 from sliding off of surface 16 when the holding means is tilted. As shown in FIG. 1, elongate members 12 prevent prosthesis 20 from sliding off of surface 16 in the forward direction. Elongate members 12 also restrict the side-to-side movement of prosthesis 20. In order to further restrict the side-to-side movement of prosthesis 20 and to prevent prosthesis 20 from sliding off of the back end of support member 14, holding means 8 also includes an upwardly extending support member 22. As shown in FIGS. 4, 5, and 6, the lower edge of upwardly extending support member 22 is attached to surface 16 at the upper end of support member 14. Upwardly extending support member 22 has an arcuate upper edge which is positionable beneath prosthesis 20. In addition to restricting the backward and sideways movement of prosthesis 20, upwardly extending support member 14 factilitates fluid circulation and drainage by partially holding (i.e., raising the back end of) prosthesis 20 above surface 16.

Embodiment 2 also includes standing means, positioned at the bottom of holding means 8, for standing the holding means in an upright position on a substantially horizontal surface. The holding means of apparatus 2 basically consists of two standing supports 24 attached to the bottom of support member 14. Standing supports 24 extend backwardly and outwardly from the bottom of support member 14. The bottom edges of standing supports 24 lie in essentially the same plane as the lower edge of sloping support member 14. Thus, the bottom edges of standing supports 24 and the lower edge of sloping support member 14 will support holding means 8 when the holding means is placed on a level surface.

As shown in FIGS. 4, 5, and 6, the upper ends of elongate members 12 are connected to rim 10 of cover 6. Thus, cover 6 provides a convenient gripping means which the user can grasp when placing holding means 8 in container 4, removing holding means 8 from container 4, and when rinsing the holding means and the prosthesis.

As is apparent, the inventive apparatus call generally be constructed using any one of numerous manufacturing techniques. For example, container 4, cover 6, and holding means 8 can be separately molded. Slots can be provided in rim 10 of cover 6 for inserting elongate members 12 in order to connect holding means 8 to cover 6. Glue can be used as necessary to more securely connect holding means 8 to cover 6.

In the inventive method, water and a denture cleanser are combined and mixed in container 4 of the inventive apparatus. Subsquently, prosthesis 20 is placed in holding means 8, holding means 8 is placed in container 4, and cover 6 is placed over the opening at the top of container 4. The amount of water added to container 4 should be an amount sufficient to at least cover prosthesis 20. The amount of denture cleanser added to container 4 should generally be an amount sufficient to clean prosthesis 20. The denture cleanser is preferably a denture powder or liquid which will quickly mix with and dissolve in the water.

The contents of the inventive apparatus are heated in a microwave for a time sufficient to provide a hot cleaning fluid. In order to protect the prosthesis from warpage, however, the cleaning fluid should not be brought to a boil. Given a typical microwave oven and assuming that the apparatus contains from about 6 to about 8 ounces of water, the contents of apparatus 2 should be microwaved for about two minutes at the oven's regular setting.

Following the heating and cleaning cycle, holding means 8, with prosthesis 20 held therein, is removed from container 4. Holding means 8 is then used to hold prosthesis 20 as prosthesis 20 is rinsed with tap water. Holding means 8, with prosthesis 20 held therein, is then placed on a level surface. Upwardly extending support 22 and apertures 18 of the inventive apparatus allow the rinse water remaining on the prosthesis 20 to quickly drain away.

Thus, the present invention is well adapted to carry out the objects and obtain the ends and advantages mentioned above as well as those inherent therein. While numerous changes may be made by those skilled in the art, such changes are encompassed within the scope of the invention as defined by the appended claims.

What is claimed is:

1. A method of cleaning a prosthesis, said prosthesis comprising a metallic portion, comprising the steps of:
   (a) placing said prosthesis, water, and an effective amount of a denture cleanser for cleansing said prosthesis in a microwave insulating device; and
   (b) then heating the contents of said microwave insulating device in a microwave oven.

2. The method of claim 1 wherein said microwave insulating device comprises:
   a container having an opening at the top thereof, said container comprising a microwave insulating material;
   a cover removably positionable over said opening, said cover comprising a microwave insulating material; and
   a holding means, removably positionable in said container, for holding said prosthesis and for facilitating fluid circulation through and under said prosthesis, said prosthesis being removably held in said holding means in step (b), said holding means comprising:
   a first upwardly extending elongate member,
   a second upwardly extending elongate member spaced apart from said first upwardly extending elongate member,
   a first support member connected between said upwardly extending elongate members and having a sloping upper surface such that said elongate members and said sloping upper surface form a restriction for gravitationally holding said prosthesis on said sloping upper surface and against said upwardly extending elongate members, and
   an upwardly extending second support member connected to said first support member and having an arcuate upper edge which is positionable beneath said prosthesis for retaining said prosthesis in said restriction and for at least partially holding said prosthesis above said sloping upper surface, wherein said container and said cover are operable for substantially completely enclosing said prosthesis such that said prosthesis can be safely microwaved in said microwave oven.

3. The method of claim 2 wherein:

said microwave insulating device further comprises standing means, positioned at the lower end of said holding means, for standing said holding means on a substantially horizontal surface and said method further comprises the steps of:
(c) removing said holding means, and said prosthesis being held therein, from said container;
(d) rinsing said prosthesis; and
(e) standing said holding means, and said prosthesis being held therein, on a substantially horizontal surface.

* * * * *